United States Patent [19]
Stefansson et al.

[11] Patent Number: 6,156,785
[45] Date of Patent: Dec. 5, 2000

[54] METHOD FOR INCREASING OXYGEN TENSION IN THE OPTIC NERVE AND RETINA

[75] Inventors: Einae Stefansson, Reykjavik, Iceland; Jens Dollerup, Lyngby; Kurt Bang, Kokkedal, both of Denmark

[73] Assignee: Merck Sharp & Dohme B.V., Netherlands

[21] Appl. No.: 09/232,973

[22] Filed: Jan. 19, 1999

Related U.S. Application Data

[60] Provisional application No. 60/072,360, Jan. 23, 1998.
[51] Int. Cl.⁷ .................................................. A61K 31/38
[52] U.S. Cl. ........................ 514/432; 514/530; 514/573; 514/913
[58] Field of Search .................................. 514/432, 913, 514/530, 573

[56] References Cited

U.S. PATENT DOCUMENTS

| | | |
|---|---|---|
| 4,386,098 | 5/1983 | Woltersdorf et al. . |
| 4,416,890 | 11/1983 | Woltersdorf . |
| 4,426,388 | 1/1984 | Woltersdorf . |
| 4,599,353 | 7/1986 | Bito . |
| 4,797,413 | 1/1989 | Baldwin et al. . |
| 4,824,857 | 4/1989 | Goh et al. . |
| 4,833,819 | 5/1989 | Bito . |
| 5,001,153 | 3/1991 | Ueno et al. . |
| 5,153,192 | 10/1992 | Dean et al. . |
| 5,240,923 | 8/1993 | Dean et al. . |
| 5,378,703 | 1/1995 | Dean et al. . |

OTHER PUBLICATIONS

Grunwald, J. E. et al., Investigative Ophthalmology & Visual Science, vol. 33, No. 3, pp. 504–507 (1992).
Harris, A. et al., Acta Opthalmologica Scandinavica, vol. 74, pp. 569–572 (1996).
Hickman, J. B. et al., Retinal Circulation, vol. 33, pp. 302–316 (1966).
Kerty, E. et al., Acta Ophthalmologica, vol. 72, pp. 401–408 (1994).
Kerty, E. et al., Acta Ophthalmologica Scandinavica, vol. 73, pp. 66–71 (1995).
Novack, R. L. et al., Exp. Eye Res., vol. 50, pp. 289–296 (1990).
Rassam, S. M. B. et al., Eye, vol. 7, pp. 697–702 (1993).
Vorstrup, S. et al., J. Clin. Invest., vol. 74, pp. 1634–1639 (1984).
T. Eysteinsson et al., Investigative Ophthalmology & Visual Science, 39(4), pp. 693 (1998).
B. Anderson, *Trans Am Ophthalmology Society* 66, pp 423–474–(1968).

*Primary Examiner*—Zohreh Fay
*Attorney, Agent, or Firm*—Sylvia A. Ayler; Mark R. Daniel

[57] ABSTRACT

There is disclosed a method for increasing retinal and optic nerve head oxygen tension by application of a composition comprising carbonic anhydrase inhibitors to the eye.

20 Claims, 8 Drawing Sheets

METHOD FOR INCREASING OXYGEN TENSION IN THE OPTIC NERVE AND RETINA

This is a non-provisional application of U.S. Ser. No. 60/072,360, filed Jan. 23, 1998.

BACKGROUND OF THE INVENTION

Glaucoma is characterized by progressive atrophy of the optic nerve and is frequently associated with elevated intraocular pressure (IOP). The treatment of glaucoma has focused on the elevated IOP and only recently has the attention been shifted more to the optic nerve, where the disease process is predominantly seen. Effective treatment of glaucoma must somehow affect the conditions and metabolism of the optic nerve to stop the atrophic process.

Due to the inaccessibility of the optic nerve, its metabolism has not been thoroughly studied (Novak and Stefansson et al., Exp. Eye Res. 50, 289–96, 1990; and Clin. Exp. Ophthalmol 228, 128–33, 1990). A few reports exist on the blood flow in the optic nerve and retina and how this is affected by glaucoma drugs, such as carbonic anhydrase inhibitors. Vorstrup and associates (Vorstrup et al., J. Clin. Invest. 74: 1634–39 (1984)) found that intravenous administration of acetazolamide increased cerebral blood flow. The flow velocity in the intracranial arteries increased whereas a decrease was observed in the ophthalmic artery together with a decrease in ocular pulsatile blood flow (Kerty, et at, Acta Ophthalmol 73: 66–71 (1995) and Acta Ophthalmol 72: 401–8 (1994)), mainly originating from the choroidal circulation. In contrast, Rassam and associates (Rassam et al., Eye 7: 697–702 (1993)) found that intravenous acetazolamide increased retinal blood flow, whereas Grunwald et al., Invest Ophthalmol. Vis Sci 33: 504–7 (1992) found no effect by oral acetazolamide on macular blood flow evaluated with the blue field entopic technique; Harris and associates (Harris et al., Acta Ophthalmol 74: 569–72 (1996)) reported that the application of one drop of dorzolamide 3% decreased the artterio-venous transit time and increased the velocity of fluorescent particles in the paramacular and peripapillary microcirculations, whereas no effect was seen on flow velocity in the retrobulbar vessels.

Ischemia of the microcirculation around the papilla is assumed to be relevant for the pathogenesis of glaucomatous damage to the nerve fiber layer. Several drugs have been tested for their influence on perfusion of the posterior pole of the eye.

The present invention relates to the use of carbonic anhydrase inhibitors to increase vitreal oxygen tension over the optic nerve notwithstanding that oxygen is a powerful retinal vasoconstrictor of the retinal vessels (Hickman & Frayser, Circulation 33, 302–316 (1966)).

DESCRIPTION OF THE DRAWINGS

FIG. 5. Optic nerve oxygen tension reading over time. Time from beginning of record is shown in minutes (and hours) on the horizontal axis and oxygen tension as percent atmosphere on the vertical axis. One minute before mark 9 seven drops of TRUSOPT® (dorzolamide 2%) is applied to the eye.

SUMMARY OF THE INVENTION

The present invention is directed to a method for increasing retinal and optic nerve oxygen tension in a patient in need thereof by application of a carbonic anhydrase inhibitor (CAI) either orally, intraveneously or topically. A preferred method is the administration of a topical carbonic anhydrase inhibitor. The invention is also directed to a method for increasing retinal and optic nerve oxygen tension in a patient in need thereof by administering a composition comprising a hypotonic solution of xanthan gum and a carbonic anhydrase inhibitor, preferably a hypotonic solution of xanthan gum and a topical carbonic anhydrase inhibitor.

Particularly, the invention relates to a method for increasing retinal and optic nerve oxygen tension by application of a carbonic anhydrase inhibitor (CAI) such as those which are described in U.S. Pat. Nos. 4,797,413, 4,386,098, 4,416,890, 4,426,388, 5,378,703, 5,240,923 and 5,153,192; and the like. Particularly preferred carbonic anhydrase inhibitors are topical carbonic anhydrase inhibitors belonging to the class having structural formula (I):

(I)

an individual diastereomer, an individual enantiomer or mixture thereof, or an ophthalmologically acceptable salt thereof, wherein:

A is carbon or nitrogen, preferably carbon;

Z is —NHR or —OR, preferably —NHR;

R is $C_{1-6}$alkyl, either straight or branched chain, preferably $C_{2-4}$alkyl such as ethyl, propyl or isobutyl;

$R^1$ is (a) hydrogen, (b) $C_{1-3}$alkyl, preferably methyl, ethyl or n-propyl, or (c) $C_{1-4}$alkoxy-$C_{1-4}$alkyl, preferably 3-methoxypropyl or ethoxymethyl; and X is —S(O)$_2$— or —C(O)—, preferably —S(O)$_2$—.

The carbon atoms to which Z and $R^1$ are bonded may be chiral. When named according to absolute configuration, e.g., (R,S) or (S,S), the first letter represents the chirality the carbon atom to which Z is bonded and the second letter represents the chirality of A when A is carbon. The carbonic anhydrase inhibitors of this invention accordingly may be used as diastereomeric mixtures or single enantiomers or as racemic mixtures. More preferred carbonic anhydrase inhibitors are dorzolamide, brinzolamide, acetazolamide, metazolamide, sezolamide described in U.S. Pat. Nos., 4,797,413, 4,386,098, 4,416,890, 4,426,388, 5,378,703, 5,240,923 and 5,153,192; and the like.

Dorzolamide, which has recently been approved under the trademark, TRUSOPT®, is the first topically effective CAI for clinical use in treating glaucoma and ocular hypertension. (S,S)-(−)-5,6-Dihydro-4-ethylamino-6-methyl-4H-thieno[2,3-b]thiopyran-2-sulfonamide-7,7-dioxide hydrochloride (dorzolamide HCl; MK507) is the active ingredient in TRUSOPT® which is prescribed for the treatment of elevated intraocular pressure in ocular hypertension, open-angle glaucoma and pseudo-exfoliative glaucoma. TRUSOPT® Ophthalmic Solution is applied as an isotonic, buffered, slightly viscous, aqueous solution of dorzolamide HCl. Each ml of TRUSOPT® 2% contains 20 mg dorzolamide (22.3 mg dorzolamide HCl). When used as monotherapy, the dose is one drop of TRUSOPT® Ophthalmic Solution in the conjunctival sac of each affected eye three times daily.

More particularly, the invention relates to a method for increasing retinal and optic nerve oxygen tension by topical application of a composition wherein the topical carbonic anhydrase inhibitor is (S,S)-(−)-5,6-dihydro-4-ethylamino-6-methyl-4H-thieno[2,3-b]thiopyran-2-sulphonamide-7,7-dioxide, or an ophthalmologically acceptable salt thereof or 2H-thieno[3,2-e]-1,2-thiazine-6-sulfonamide-4-(ethylamino)-3,4-dihydro-2-(3-methoxypropyl)-1,1-dioxide or an ophthalmologically acceptable salt thereof. Other aspects of the invention will become apparent upon review of the complete application.

DETAILED DESCRIPTION OF THE INVENTION

The present invention is directed to a method for increasing retinal and optic nerve oxygen tension by application of a carbonic anhydrase inhibitor and preferably by application of a topical carbonic anhydrase inhibitor. A more preferred method is the application of a composition comprising a hypotonic solution of xanthan gum and a topical carbonic anhydrase inhibitor.

The present invention is based upon the finding that CAIs can preserve or benefit vision by increasing oxygen tension in the retina and optic nerve which when coupled with the attending increase in ocular blood flow benefits optic nerve health.

Research was done using dorzolamide and acetazolamide as the carbonic anhydrase inhibitors. It is a known compound useful as a carbonic anhydrase inhibitor and for the reduction of intraocular pressure.

In the compositions of the present invention the concentration of xanthan gum comprises about 0.1 to 2% (w/w), preferably 0.4 to 0.7% (w/w). Particularly preferred is KELTROL™ T xanthan gum from Monsanto Performance Materials.

Xanthan gum is a high molecular weight polysaccharide gum obtainable from the aerobic fermentation of a carbohydrate with bacteria of the genus Xanthomonas, especially *Xanthomonas campestris*. Each xanthan gum repeat unit contains five sugar residues: two glucose, two mannose and one glucuronic acid. The polymer backbone consists of four β-D-glucose units linked at the 1 and 4 positions. Trisaccharide side chains on alternating anhydroglucose units distinguish xanthan gum from cellulose. Each side chain comprises a glucuronic acid residue between two mannose units. At most of the terminal mannose units is a pyruvate moiety.

Xanthan gum solutions are pseudoplastic. In other words, when shear stress is increased, the viscosity is progressively reduced. Upon reduction of the shear, total viscosity is recovered almost instantaneously. This behavior results from the high-molecular-weight molecule which forms complex molecular aggregates through hydrogen bonds and polymer entanglement. Also, this highly ordered network of entangled, stiff molecules accounts for the high viscosity observed at low shear rates. Shear thinning results from disaggregation of this network and alignment of individual polymer molecules in the direction of shear force. However, when the shearing ceases, aggregates re-form rapidly. As a result of its helical conformation, xanthan gum viscosity is relatively insensitive to temperature changes below the transition temperatures and to differences in ionic strength and pH. Xanthan gum solutions do not therefore have any liquid-gel phase transition properties, hence xanthan gum is not suitable for use in the formulation of in situ gelling solutions.

The results of the present invention suggest that the high degree of pseudoplasticity, which is independent of concentration, appears to be important in contributing to the unusual ocular penetration properties of the hypotonic formulation of xanthan gum.

Xanthan gum is commercially available, for example, under the tradename KELTROL™ from Monsanto Performance Materials, a unit of Monsanto Company, St. Louis, Mo. 63167, USA.

Following administration of the composition to the conjunctival sac of a patient's eye, there is no liquid-gel phase transition. The advantageous enhancement in ocular bioavailability of the topical carbonic anhydrase inhibitor is achieved through the unique combination of the properties of the hypotonic solution of xanthan gum.

The topical carbonic anhydrase inhibitors of use in the present invention include those compounds described in U.S. Pat. Nos. 4,797,413, 4,386,098, 4,416,890, 4,426,388, 5,378,703, 5,240,923 and 5,153,192; and the like. Preferred topical carbonic anhydrase inhibitors are the class of compounds of the structural formula (I):

(I)

an individual diastereomer, an individual enantiomer or mixture thereof, or an ophthalmologically acceptable salt thereof, wherein:

A is carbon or nitrogen, preferably carbon;

Z is —NHR or —OR, preferably —NHR;

R is $C_{1-6}$alkyl, either straight or branched chain, preferably $C_{2-4}$alkyl such as ethyl, propyl or isobutyl;

$R^1$ is
(a) hydrogen,
(b) $C_{1-3}$alkyl, preferably methyl, ethyl or n-propyl, or
(c) $C_{1-4}$alkoxy-$C_{1-4}$alkyl, preferably 3-methoxypropyl or ethoxymethyl; and X is —S(O)$_2$— or —C(O)—, preferably —S(O)$_2$—.

The carbon atoms to which Z and $R^1$ are bonded may be chiral. When named according to absolute configuration, e.g., (R,S) or (S,S), the first letter represents the chirality the carbon atom to which Z is bonded and the second letter represents the chirality of A when A is carbon. The carbonic anhydrase inhibitors of this invention accordingly may be used as diastereomeric mixtures or single enantiomers or as racemic mixtures.

Preferred topical carbonic anhydrase inhibitors for use in the present invention are compounds of formula (I), above, wherein A is carbon; and wherein R is —CH$_2$CH$_3$ and $R^1$ is —CH$_3$; or R is —CH$_2$CH$_2$CH$_3$ and $R^1$ is —CH$_2$CH$_2$CH$_2$OCH$_3$; or R is —CH$_2$CH$_3$ and $R^1$ is —CH$_2$CH$_2$CH$_3$; or R is —CH$_2$CH$_2$(CH$_3$)$_2$ and $R^1$ is hydrogen; or R is —CH$_2$CH$_3$ and $R^1$ is —CH$_2$OCH$_2$CH$_3$; and carbons 4 and 6 of the topical carbonic anhydrase inhibitor both have S absolute stereochemical configuration.

More preferred carbonic anhydrase inhibitors are dorzolamide, brinzolamide, acetazolamide, metazolamide described in U.S. Pat. Nos., 4,797,413, 4,386,098, 4,416,890, 4,426,388, 5,378,703, 5,240,923 and 5,153,192; and the like. Dorzolamide, which has recently been approved under the trademark, TRUSOPT®, is the first topically effective CAI for clinical use.

Most preferred topical carbonic anhydrase inhibitors are (S,S)-(–)-5,6-dihydro-4-ethylamino-6-methyl-4H-thieno[2,3-b]thiopyran-2-sulphonamide-7,7-dioxide, or an ophthalmologically acceptable salt thereof and 2H-thieno[3,2-e]-1,2-thiazine-6-sulfonamide-4-(ethylamino)-3,4-dihydro-2-(3-methoxypropyl)-1,1-dioxide or an ophthalmologically acceptable salt thereof.

A particularly preferred topical carbonic anhydrase inhibitor is dorzolamide, especially as its hydrochloride salt.

The concentration of TCAI in the present invention is about 0.05 to about 5% (w/w), usually about 0.5 to about 3% (w/w), and is administered one to three times daily, preferably one to two times daily, to each affected eye.

The novel method of this invention comprises the topical ocular administration of about 0.025 to about 5 mg per day, preferably about 0.25 to 3 mg per day, of the topical carbonic anhydrase inhibitor to each eye. Alternatively, the invention comprises the intravenous administration of about 5 mg to 600 mg of the carbonic anhydrase inhibitor to each affected eye.

As a unit dosage, between about 0.025 and about 2.5 mg, preferably between 0.25 and 1.5 mg, of the topical carbonic anhydrase inhibitor is applied to each eye. Alternatively, as a unit dosage, between about 5 mg to about 250 mg, of the carbonic anhydrase inhibitor is applied intravenously to each eye.

Conventional ophthalmic solutions are usually prepared as isotonic solutions using tonicity adjusting agents such as potassium chloride, sodium chloride, mannitol, dextrose and glycerin. An isotonic solution will have a freezing point depression of approximately –0.54° C. Tonicity may also be measured by the osmolality of the solution, an isotonic solution having an osmolality of about 290 milliosmoles per kilogram (mOs/kg).

It is a characteristic of the ophthalmic compositions of the present invention that they are hypotonic solutions, with a freezing point depression between about –0.28° C. and –0.4° C., and preferably between about –0.31° C. and –0.37° C.

Alternatively, the hypotonicity of the ophthalmic solutions of the present invention is between about 150 and 215 mOs/kg, and preferably between 170 and 200 mOs/kg.

According to a further aspect of the present invention, there is provided a novel method for increasing retinal and optic nerve oxygen tension by application of a carbonic anhydrase inhibitor, preferably by topical application of a composition comprising a hypotonic solution of xanthan gum, a therapeutically effective amount of a topical carbonic anhydrase inhibitor and a therapeutically effective amount of a β-adrenergic receptor blocking agent. Suitable β-adrenergic receptor blocking agents include betaxolol, bufetolol, carteolol, levobunolol, metipranolol, and timolol, or an ophthalmologically acceptable salt thereof. A particularly preferred β-adrenergic receptor blocking agent is timolol maleate.

Such compositions preferably comprise about 0.05 to 5% (w/w) of the topical carbonic anhydrase inhibitor, usually about 0.5 to 3% (w/w), preferably about 0.7% to about 2.0% (w/w) and about 0.01 to 1% (w/w) of the β-adrenergic receptor blocking agent, preferably about 0.1 to 0.5% (w/w) to be administered once or twice a day to each affected eye.

Thus, a further novel method of this invention comprises the topical ocular administration of about 0.025 to 5 mg per day, preferably about 0.25 to 3 mg per day, of the topical carbonic anhydrase inhibitor and about 0.005 to 1 mg per day, preferably about 0.05 to 0.5 mg per day, of the β-adrenergic receptor blocking agent to each eye.

As a unit dosage, between 0.005 and 0.5 mg of the β-adrenergic receptor blocking agent, and preferably between 0.05 and 0.25 mg of the β-adrenergic receptor blocking agent, is applied to each eye.

The pH of the composition ranges from about 5.0 to about 7.5, preferably about 5.5 to about 7.0.

According to a further aspect of the present invention, there is provided a novel method for increasing retinal and optic nerve oxygen tension by application of a carbonic anhydrase inhibitor, preferably by application of a composition comprising a hypotonic solution of xanthan gum, a therapeutically effective amount of a topical carbonic anhydrase inhibitor and a therapeutically effective amount of a prostaglandin, prostaglandin derivative or pharmaceutically acceptable salt thereof, such as those described in U.S. Pat. Nos. 4,883,819, 4,824,857, 5,001,153 and 4,599,353. Suitable prostaglandins include 13,14-dihydro-15(R)-17-phenyl-18,19,20-trinor-PGF2α esters, or 13, 14-dihydro-15-keto-20-ethyl-PGF2α isopropryl esters, or an ophthalmologically acceptable salt thereof.
Preferred prostaglandins are:
11-pivaloyl prostaglandin F2α hydroxyethyl ester,
(+)-(Z)-sodium-7-[1R, 2R, 3R, 5S)-3,5-dihydroxy-2-[(E)-1-octenyl]cyclopentyl]-5-heptenoate sesquihydrate,
[1α,2β,3α, 5α]methyl-5-cis-2-(phenylethylsulfonamidomethyl)-3,5-dihydroxycyclopentyl heptenoate,
(+-)-5-[6-(1-hydroxy)hexyl)-1,3-benzodioxol-5-yl]-pentanol, 15-pivaloyl PGFα,
7-[3α,5α dihydroxy-2-(3a-hydroxy-5--1E-pentenyl) cyclopentyl]-5Z-heptenoic acid,
isopropyl (Z)-7-[(1R,2R,3R,5S)-3,5-dihydroxy-2-[(3R)-3-hydroxy-5-phenylpentyl]cyclopentyl]-5-heptenoate or
13,14-dihydro-15-keto-20-ethyl-PGF2α isopropyl ester trimethylphenol-1-acetate.

Most preferred prostaglandins are isopropyl (Z)-7-[(1R, 2R,3R,5S)-3,5-dihydroxy-2-[(3R)-3-hydroxy-5-phenylpentyl]cyclopentyl]-5-heptenoate, (+)-(Z)-sodium-7-[1R, 2R, 3R, 5S)-3,5-dihydroxy-2-[(E)-1-octenyl] cyclopentyl]-5-heptenoate sesquihydrate, or 13,14-dihydro-15-keto-20-ethyl-PGF2α isopropyl ester trimethylphenol-1-acetate.

The ophthalmic formulations of this invention comprise about 0.025 to 5% (w/w) of the carbonic anhydrase inhibitors discussed herein, preferably 5,6-dihydro-4-ethylamino-6-methyl-4H-thieno-[2,3-b]thiopyran-2-sulfonamide-7,7 dioxide hydrochloride or 2H-thieno[3,2-e]-1,2-thiazine-6-sulfonamide-4-(ethylamino)-3,4-dihydro-2-(3-methoxypropyl)-1,1-dioxide and their trans and cis enantiomers, or an ophthalmologically acceptable salt thereof, including racemic material, usually about 0.5 to 3% (w/w) and more preferably about 0.7 to about 2% (w/w) and about 0.005 to 2.0% (w/w), preferably about 0.1 to 1% (w/w) of the prostaglandin or prostaglandin derivatives discussed herein, preferably 13,14-dihydro-15(R)-17-phenyl-18,19,20-trinor-PGF2a esters or 13,14-dihydro-15-keto-20-ethyl-PGF2α isoproptyl esters, and more preferably isopropyl (Z)-7-[(1R,2R,3R,5S)-3,5 -dihydroxy-2-[(3R)-3-hydroxy-5-phenylpentyl]cyclopentyl]-5-heptenoate, or 13,14-dihydro-15-keto-20-ethyl-PGF2α isopropyl ester trimethylphenol-1-acetate, to be administered on a 1 to 2 times a day schedule.

A novel method of this invention comprises the topical ocular administration of about 0.025 to about 5 mg per day, preferably about 0.25 to about 3 mg per day of a carbonic anhydrase inhibitor and concomitant, prior, or previous administration of about 0.005 to 2 mg per day, preferably about 0.1 to 1.0 mg per day, of prostaglandin or prostaglandin derivative to each eye, about 1 to about 2 times a day.

Suitable subjects for the administration of the formulation of the present invention include primates, man and other animals, particularly man and domesticated animals such as cats and dogs.

The pharmaceutical preparation may contain non-toxic auxiliary substances such as antibacterial components which are non-injurious in use, for example, thimerosal, benzalkonium chloride, methyl and propyl paraben, benzyldodecinium bromide, benzyl alcohol, or phenylethanol; buffering ingredients such as sodium chloride, sodium borate, sodium acetate, sodium citrate, or gluconate buffers; and other conventional ingredients such as sorbitan monolaurate, triethanolamine, polyoxyethylene sorbitan monopalmitylate, ethylenediamine tetraacetic acid, and the like.

The following examples of ophthalmic compositions are given by way of illustration.

EXAMPLE 1

| SOLUTION COMPOSITION | A | B |
| --- | --- | --- |
| (S,S)-(-)-5,6-Dihydro-4-ethylamino-6-methyl-4H-thieno[2,3-b]thiopyran-2-sulfonamide-7,7-dioxide monohydrochloride | 2.226% | 2.226% |
| Sodium Chloride | 0.2% | 0.2% |
| Benzalkonium Chloride | 0.0075% | 0.0075% |
| Sodium hydroxide | QS pH 5.6 | pH 5.6 |
| Purified Water | QS 100% | 100% |

The active compound, sodium chloride and benzalkonium chloride were dissolved in water for injection. The pH of the composition was adjusted to 5.6 by addition of 0.2 N sodium hydroxide solution, and water for injection was added until the weight of composition was equal to 75 parts of the final weight (Example 1A) or 65 parts of the final weight (Example 1B). The composition was sterilised by filtration, and the solution flushed with sterile nitrogen. The solution was aseptically subdivided into sterile vials and sealed.

EXAMPLE 2

| SOLUTION COMPOSITION | A | B |
| --- | --- | --- |
| (S,S)-(-)-5,6-Dihydro-4-ethylamino-6-methyl-4H-thieno[2,3-b]thiopyran-2-sulfonamide-7,7-dioxide monohydrochloride | 2.226% | 2.226% |
| Xanthan Gum | 0.5% | 0.7% |
| Sodium Chloride | 0.2% | 0.2% |
| Benzalkonium Chloride | 0.0075% | 0.0075% |
| Sodium hydroxide | QS pH 5.6 | pH 5.6 |
| Purified Water | QS 100% | 100% |

The active compound, sodium chloride and benzalkonium chloride were dissolved in water for injection. The pH of the composition was adjusted to 5.6 by addition of 0.2 N sodium hydroxide solution, and water for injection was added until the weight of composition was equal to 75 parts of the final weight (Example 2A) or 65 parts of the final weight (Example 2B). The composition was sterilised by filtration, and the solution flushed with sterile nitrogen. Then a clarified, steam sterilised concentrate of 2% xanthan gum was added to the solution of drug and the obtained solution was homogenised by stirring. The solution was aseptically subdivided into sterile vials and sealed.

EXAMPLE 3

| SOLUTION COMPOSITION | |
| --- | --- |
| (S,S)-(-)-5,6-dihydro-4-ethylamino-6-methyl-4H-thieno[2,3-b]thiopyran-2-sulfonamide-7,7-dioxide monohydrochloride | 2.226% |
| (S)-(-)-1-(tert-butylamino)-3-[(4-morpholino-1,2,5-thiadiazol-3-yl)oxy]-2-propanol maleate | 0,684% |
| Xanthan Gum | 0.5% |

-continued

| SOLUTION COMPOSITION | |
|---|---|
| Sodium Chloride | 0.15% |
| Sodium Hydroxide | QS pH 5.6 |
| Benzalkonium Chloride | 0.0075% |
| Purified Water | QS 100% |

The active compounds, sodium chloride and benzalkonium chloride are dissolved in water for injection. The pH of the composition is adjusted to pH 5.6 by addition of sodium hydroxide, and water for injection is added until the weight of the composition was equal to 75 parts of the final weight. The composition is sterilised by filtration, flushing with sterile nitrogen. Then a clarified, steam sterilised concentrate of 2% xanthan gum is added to the solution of the drug and the obtained solution is homogenised by stirring. The solution is aseptically subdivided into sterile vials and sealed.

EXAMPLE 4

Examining Oxygen Tension of Optic Nerve ($ONPO_2$)

Danish agricultural pigs (landrace), 25–33 kg in weight and brought up in specific pathogen free environment, were used. Their treatment was supervised by a veterinarian and followed the decrees of the ARVO Statement for the use of animals in ophthalmic and vision research. All experiments were conducted during daytime. The pigs were anaesthetised with midazolam (dormicum®) and ketamine followed by intravenous application of 250 mg mebumal, fentanylum (Haldid®, Jansen Cilag), 0.5 mg an hour, pancuron bromide (Pavulon®, Organon Technica, Sweden) 16 mg an hour, mebumal (Hospital Pharmacies, Denmark) 50 mg per ml as needed and atropine as needed. The right pupil was dilated with 1% tropicamide eye drops (Mydriacyl®) and 2.5% phenylephrine eye drops. A arterial line was placed in a femoral artery for continuous measurement of blood pressure and intermittent blood gas analysis. A venous line was placed in a femoral vein for continuous infusion of the anaesthetics and saline as needed. A rectal thermoprobe provided continuous reading of body temperature.

The pig was secured laterally on an operating table and a speculum was placed between the right eyelids. A conjunctival peritomy was performed and 3-0 silk sutures placed under the rectus muscle tendons to immobilise the eye. A sclerotomy was made 2.5 mm behind the limbus in the superonasal quadrant and a cannula placed, through which the polarographic electrode was advanced into the vitreous cavity. The electrode was held in a micromanipulator (Stoelting Inc. USA) and placed in the vitreous humour approximately 0.5 mm over the optic disc in an area not covered by the large vessels. The entire operation was performed using a Zeiss operating microscope and the electrode was placed using an indirect ophthalmoscope or the microscope and a flat corneal contact lens.

A silver-silver chloride reference electrode was placed in the conjunctival sac of the same (right) eye and kept moist with saline. The polarographic oxygen meter consists of a 100 micrometer platinum-iridium electrode inside a 20 gauge needle (Model 761), a silver-silver chloride reference electrode and a chemical microsensor (Model 1251, Diamond Electrotech Inc., Ann Arbor Mich., USA). The recording system was calibrated before and after each experiment in a calibration cell (Diamond Electrotech. Inc.) at 37 degrees Celsius in 0.9% saline using 100% $N_2$, 5.0% $O_2$–95% $N_2$ and 20.000% $O_2$–80% $N_2$ (provided by AGA Inc. Denmark). The barometric pressure was monitored, and the oxygen tension recordings were adjusted for barometric pressure, and expressed as mmHg.

The experiments were all run with typical indoor illumination (white fluorescent light tubes (Philips TLM 40W/29RS)). The ambient light intensity at the level of the pig's eye was measured with a Mavolux digital light meter (Gossen GmbH, Germany) and found to be 497 lux or 6 watt per square meter.

Arterial blood samples were obtained at regular intervals and arterial $PO_2$, pH and $PCO_2$ were measured with a ABL 605 blood gas analyser (Radiometer, Denmark) (table 1). Arterial blood pressure, electrocardiogram and rectal temperature were monitored continuously and it was verified that these values were within normal limits. The output of the $PO_2$ electrometer, together with continuous recordings of the arterial blood pressure and the electrocardiogram, was digitised on line with a MacLab 4/e analog-digital converter (AD Instruments Pty., Australia). The digitised recordings were fed into a power Macintosh computer. Data were displayed and analysed with the Chart v3.5.4/s software (AD Instruments Pty, Australia) and printed on an Apple LaserWriterII printer.

Each experiment was begun with the animal breathing 100% oxygen. Once a stable $ONPO_2$ level was obtained the breathing mixture was changed to air, containing 21% oxygen, and a stable level obtained again. In some experiments the breathing mixture was changed to 20.000% $O_2$ followed by 5.19% $CO_2$, 19.9% $O_2$ ($N_2$ to balance), followed by 20.000% $O_2$. The test drug was then administered by intravenous injection into the femoral line. Saline injections (20 ml intravenous) were done as controls. Dorzolamide (4%, MSD Inc., 6–500 mg doses) or acetazolamide (Diamox, Lederle Inc.) 15–500 mg were injected intravenously.

A laser doppler probe (Periflux 4001, Master, Perimed AB, Sweden) for measurement of blood flow was placed through the pars plana transvitreally onto the optic disc near the oxygen electrode, to obtain simultaneous recordings of optic nerve oxygen tension and blood flow. In three experiments the intraocular pressure was fixed at 20 cm of saline (15 mmHg) with a needle in the anterior chamber connected to a saline reservoir, and recorded with a pressure transducer, while dorzolamide was injected intravenously and $ONPO_2$ recorded. Means and standard deviations were calculated and differences evaluated with a paired Student's t-test.

RESULTS

The Effects of Inhaled $O_2$ and $CO_2$.

Figure 1:
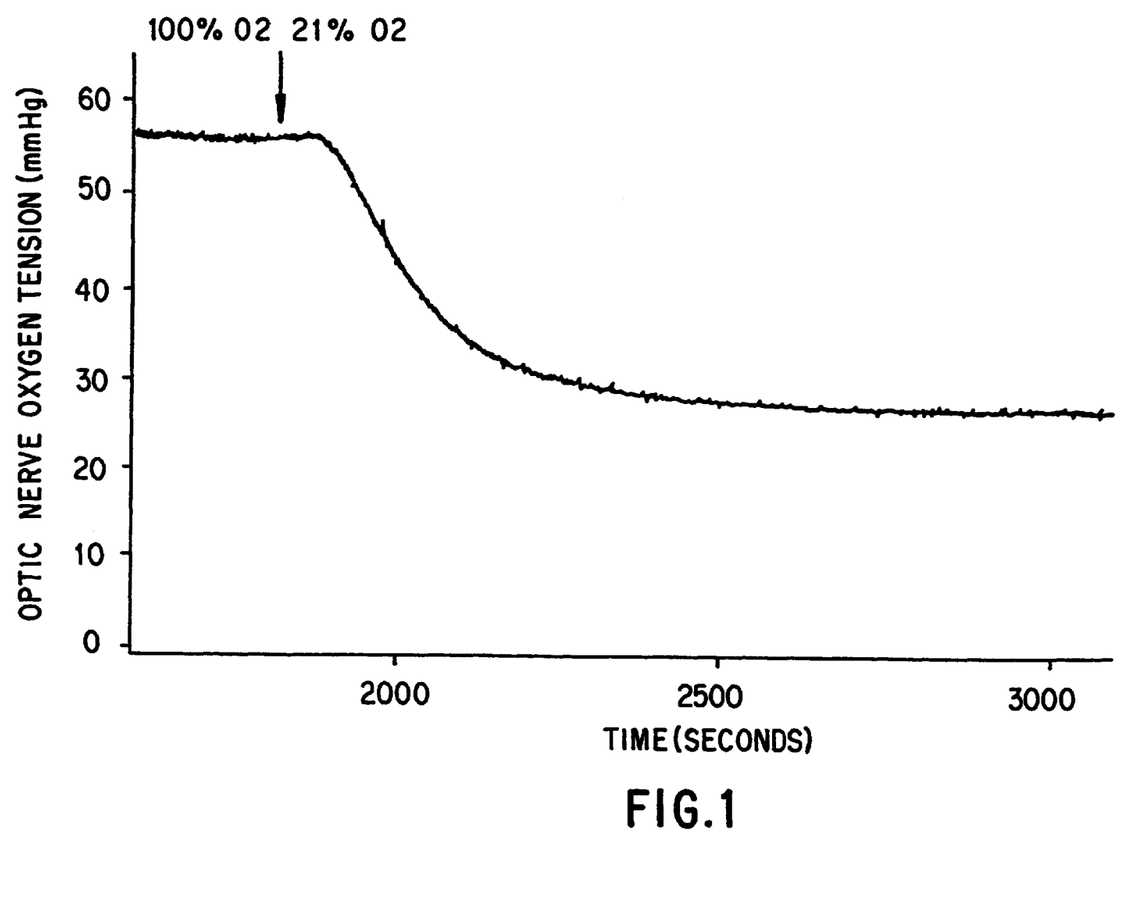
FIG. 1. Optic nerve oxygen tension reading over time. Time from beginning of record is shown in seconds on the horizontal axis and oxygen tension as mmHg on the vertical axis. At the arrow the breathing mixture is change from 100% $O_2$ to air (21% $O_2$).
Figure 2:
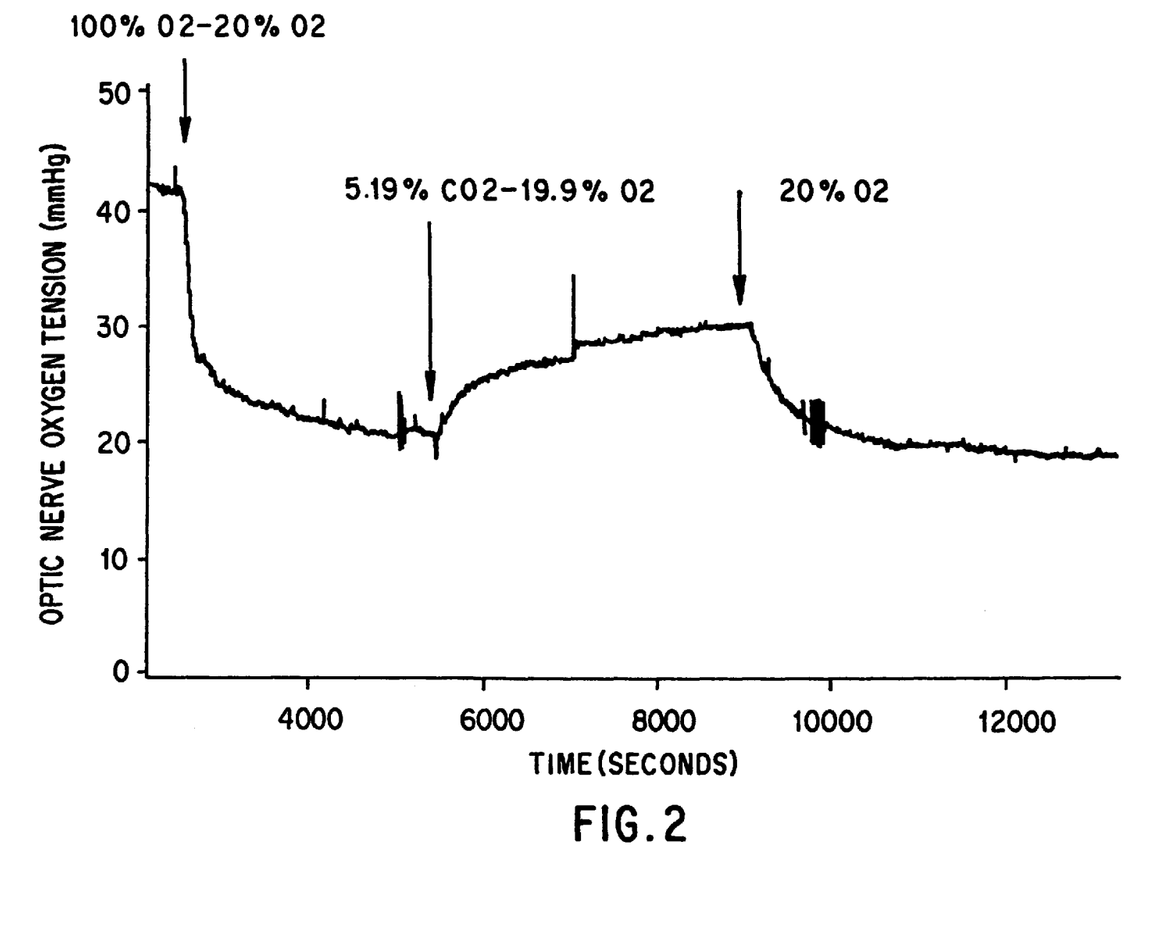
FIG. 2. Optic nerve oxygen tension reading over time. Time from beginning of record is shown in seconds on the horizontal axis and oxygen tension as mmHg on the vertical axis. The middle arrow indicates when the breathing mixture was switched to 5.19% $CO_2$ and 19.9% $O_2$. The arrow on the right indicates when the breathing mixture was returned to 20% oxygen ($N_2$ to balance).

In the initial set of experiments the oxygen tension at the optic nerve head while the animals inhaled various concentrations of oxygen, and $CO_2$, was examined. Stable, continuous and reproducible recordings of $ONPO_2$ were obtained for up to 8 hours in pigs. The mean $ONPO_2$ was 24.1±11.6 mmHg when breathing room air, and 50.7±29.3 mmHg while the animals were breathing 100% $O_2$, (n=15; p<0.001). FIG. 1 shows an experinient were the animal first inhaled 100% $O_2$. When the oxygen content was reduced to 21% $O_2$, there was an immediate reduction in the $ONPO_2$. In four experiments the breathing mixture was switched from 20% $O_2$ to a mixture of 5.19% $CO_2$ and 19.9% $O_2$ ($N_2$ to balance). In response to breathing 5.19% $CO_2$ the $ONPO_2$ changed from 20.8±5.6 mmHg to 28.9±3.6 mmHg (n=4, p<0.001). An example of this increase in $ONPO_2$ is illustrated in FIG. 2, which also shows that almost immediately upon returning to 20% $O_2$–80% $N_2$, the $ONPO_2$ returned to its value before breathing $CO_2$. As shown in Table 2, $CO_2$ breathing significantly lowered the arterial pH, and also raised the arterial $PCO_2$, but had no significant effect on the arterial $PO_2$.

The Effects of Carbonic Anhydrase Inhibition.

In another set of experiments the effects of inhibiting carbonic anhydrase activity by intravenous injection of two carbonic anhydrase inhibitors, commonly used as treatment for glaucoma were examined. Polarographic oxygen electrodes were placed in the vitreous humour 0.5 mm above the optic disc in anaesthetized pigs. Arterial blood pressure and gasses were monitored and $ONPO_2$ was recorded continously with various breathing gasses. The test drug was than administered by intravenous injection in the femoral line or by topical application on the eye. Saline injections (20 ml intravenous) or topical application on the eye were done as controls. Dorzolamide (4% MSD Inc., 500, 250, or 125 mg) was injected intravaneously or topical on the eye was 4% solution or 2% (TRUSOPT®, MSD, Inc.) solution. Acetazolamide (Diamox Lederle Ind.) 500 mg, 250 mg, 125 mg or 31 mg were injected intravenously. The carbonic anhydrase inhibitors, dorzolamide and acetazolamide raised the optic nerve oxygen tension by about 25–60% (n=4, p=0.046) and 15–35% (n=4, p=0.005), respectively.

Figure 3:
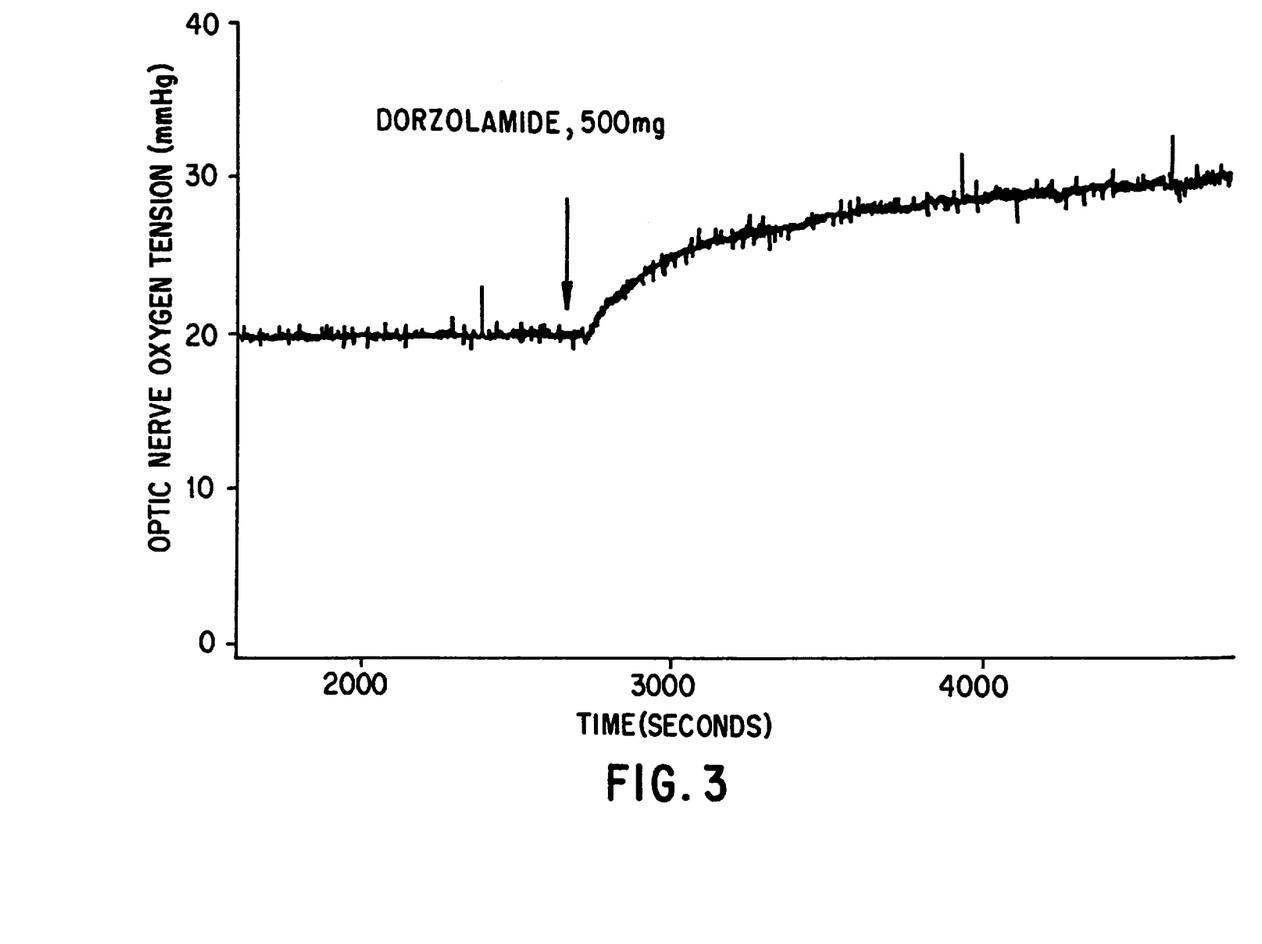
FIG. 3. Optic nerve oxygen tension reading over time. Time from beginning of record is shown in seconds on the horizontal axis and oxygen tension as mmHg on the vertical axis. At the arrow 500 mg of dorzolamide was given.
Figure 4:
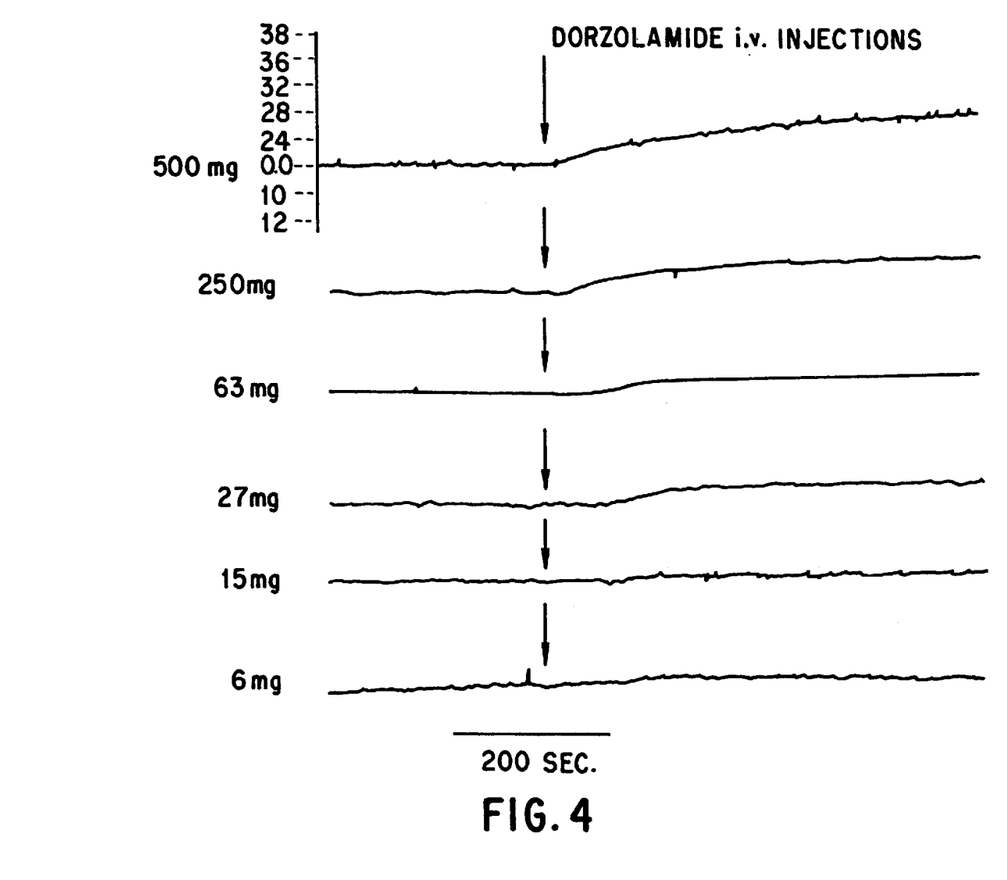
FIG. 4. The effects of intravenous dorzolamide on optic nerve oxygen tension. The figure shows six independent recordings where different amounts of dorzolamide were given intravenously at the times indicated by the arrows. Time is shown (in seconds) on the horizontal axis and oxygen tension (mmHg) on the vertical axis.
Figure 5:
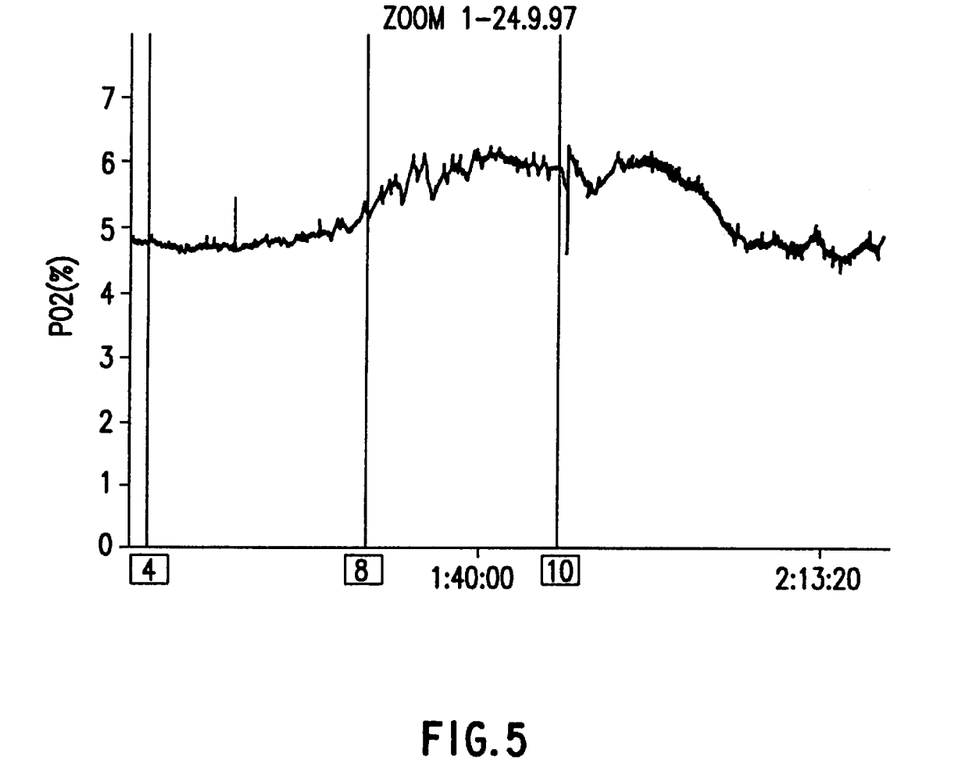
FIG. 5. Optic nerve oxygen tension reading over time. Time from beginning of record is shown in minutes (and hours) on the horizontal axis and oxygen tension as percent atmosphere on the vertical axis. One minute befores mark 9 seven drops of TRUSOPT® (dorzolamide 2%) is applied to the eye.

Specifically, intravenous injections of 500 mg dorzolamide raised the $ONPO_2$ from 16.4±6.1 mmHg to 26.9±12.2 mmHg, or 52.5%±21.2% (n=5; p=0.017), as illustrated by a typical expetiment (FIG. 3). As shown in Table 2, dorzolamide significantly lowered the arterial pH, and also raised the arterial $PCO_2$, but had no significant effect on the arterial $PO_2$. The effect of dorzolamide on $ONPO_2$ is dependent on the dose injected, and an effect is seen with injections of 6 to 500 mg (FIG. 4). The magnitude and time course of the response is related to dosage. FIG. 5 shows the results of topical administration. One minute before mark 9 seven drops of TRUSOPT® (dorzolamide 2%) is applied to the eye.

Figure 6:
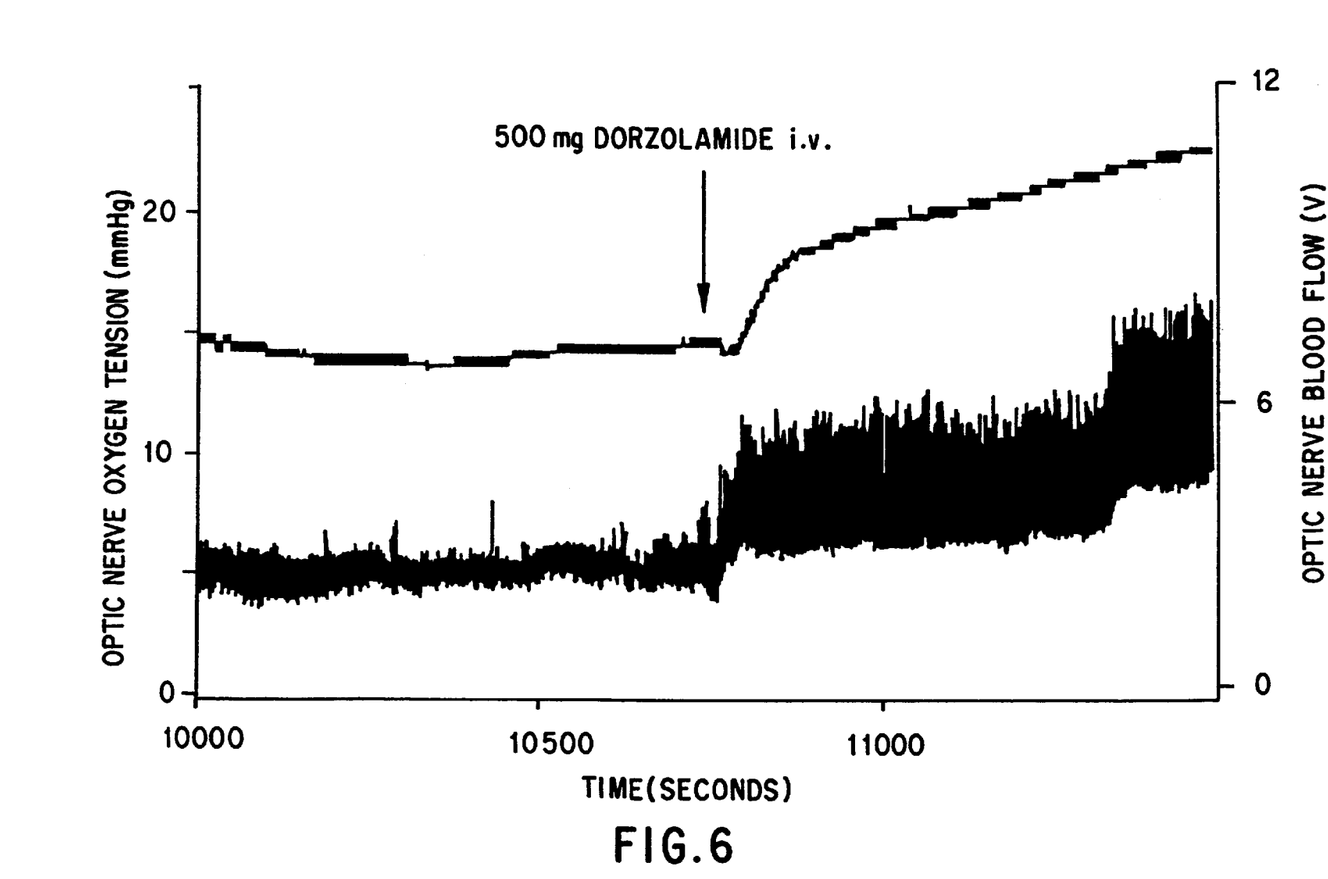
FIG. 6. The effects of 500 mg intravenous dorzolamide on the optic nerve oxygen tension (expressed as mmHg on the left vertical axis) and the optic nerve blood flow (expressed as volts on the right vertical axis), recorded simultaneously from the same optic nerve. Time from the beginning of recording from this optic nerve is shown on the horizontal axis (in seconds).

In some experiments, optic nerve blood flow was recorded concurrently with ONPO2, with a laser Doppler probe (FIG. 6). In this experiment 500 mg dorzolamide was injected intravenously. Both ONPO2 and optic nerve blood flow rose simultaneously shortly after infusion of the drug.

Figure 7:
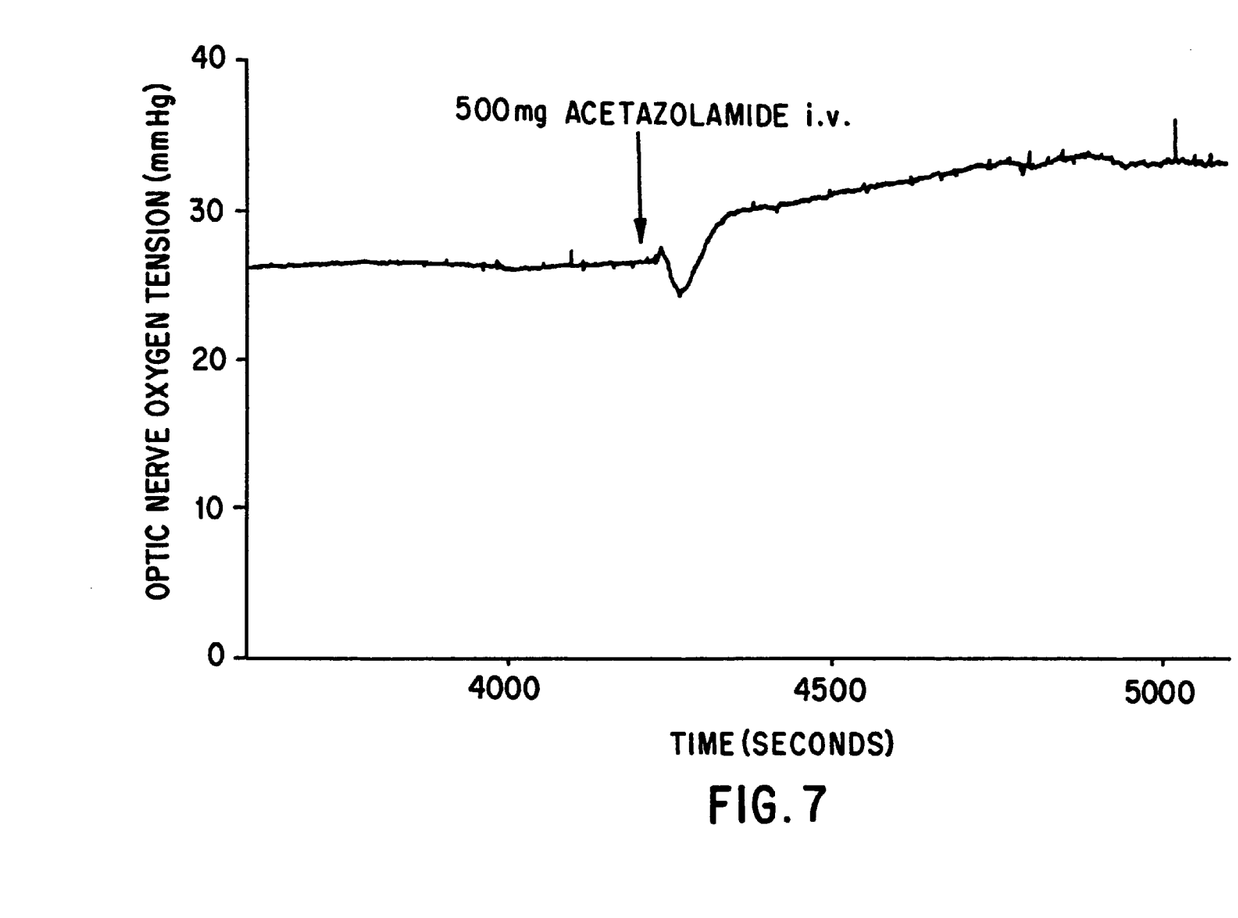
FIG. 7. The effect of intravenous acetazolamide on optic nerve oxygen tension. Time from beginning of record is shown (in seconds) on the horizontal axis and oxygen tension (as mmHg) on the vertical axis. At the point indicated by the arrow an intravenous injection of 500 mg acetazolamide was given.

Intravenous injections of 500 mg acetazolamide raised the ONPO2 from 23.6±9.5 mmHg to 30.9±10.0 mmHg(n=6, p=0.0008). FIG. 7 shows a typical response to intravenous injection of acetazolaimde. A transient lowering of arterial blood pressure follows the acetazolamide injection and corresponds in time to the transient dip in the ONPO2 recording. Control injections and topical application of saline had no effect on ONPO2.

Figure 8:
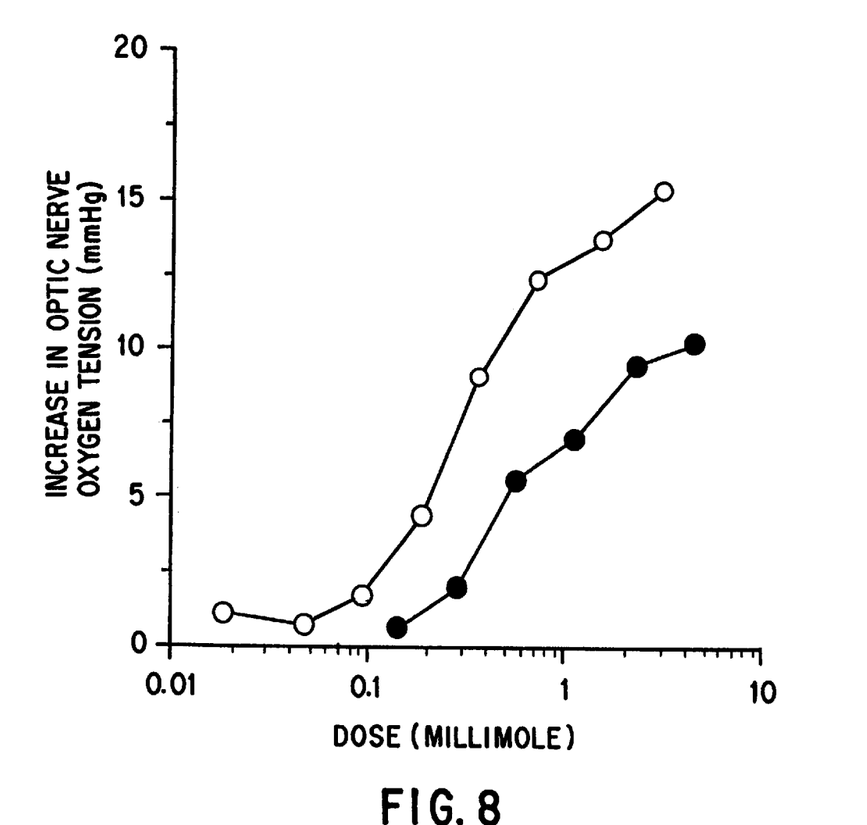
FIG. 8. Dose-response relationship between intravenous acetazolamide (closed circles) and dorzolamide (open circles), expressed in log millimole, and increase in optic nerve oxygen tension (expressed as change in mmHg).

The effects of acetazolamide and dorzolamide on ONPO2 are dose dependent, and dorzolamide is more potent as demonstrated by FIG. 8.

TABLE 1 physiological parameters in experimental pigs

| Parameter | Mean | st. dev. | max, | min. |
|---|---|---|---|---|
| Heart rate (per minute) | 113.6 | 33.2 | 187 | 65 |
| Blood pressure (mmHg) | 100.9 | 16.2 | 127 | 75 |
| pH | 7.61 | 0.042 | 7.66 | 7.49 |
| $pCO_2$ (kpa): | 4.04 | 0.471 | 5.55 | 3.3 |
| $pO_2$ in air (kPa) | 13.67 | 1.46 | 17.43 | 10.57 |
| $pO_2$ in 100% $O_2$ (kp&) | 70.13 | 4.85 | 76.45 | 61.54 |
| Rectal Temp (C.) | 38.28 | 1.09 | 40.7 | 36.7 |
| Electrode drift (%$O_2$ per hour) | 0.033 | 0.061 | 0.214 | 0.006 |

TABLE 2

Alterations in arterial blood gases

| | Before | | After | | Before | | After | | Before |
|---|---|---|---|---|---|---|---|---|---|
| | Mean | SD | Mean | SD | Mean | SD | Mean | SD | Mean |
| $CO_2$ breathing | 7.62 | 0.05 | 7.42 | 0.03* | 13.84 | 1.1 | 14.13 | 0.93 | 3.96 |
| acetazolamide 500 mg | 7.62 | 0.01 | 7.49 | 0.03* | 14.79 | 1.67 | 13.62 | 1.5 | 3.84 |
| dorzolamide 500 mg | 7.57 | 0.05 | 7.43 | 0.05* | 12.96 | 1.58 | 12.36 | 0.7 | 4.42 |

*p < 0.001

What is claimed is:

1. A method for increasing the optic nerve and retinal oxygen tension which comprises applying to the eye an effective amount of a carbonic anhydrase inhibitor.

2. A method for increasing the optic nerve and retina oxygen tension which comprises applying to the eye an effective amount of a composition comprising a hypotonic solution of 0.1 to 2% (w/w) of xanthan gum and 0.5 to 5% (w/w) of a carbonic anhydrase inhibitor.

3. The method according to claim 2 wherein the composition is applied topically.

4. The method according to claim 3 wherein the carbonic anhydrase inhibitor is a compounds of the structural formula (I):

an individual diastereomer, an individual enantiomer or mixture thereof, or an ophthalmologically acceptable salt thereof, wherein:
  A is carbon or nitrogen, preferably carbon;
  Z is —NHR or —OR, preferably —NHR;
  R is $C_{1-6}$alkyl, either straight or branched chain, preferably $C_{2-4}$alkyl such as ethyl, propyl or isobutyl;
  $R^1$ is
    (a) hydrogen,
    (b) $C_{1-3}$alkyl, preferably methyl, ethyl or n-propyl, or
    (c) $C_{1-4}$alkoxy-$C_{1-4}$alkyl, preferably 3-methoxypropyl or ethoxymethyl; and
  X is —S(O)$_2$— or —C(O)—, preferably —S(O)$_2$—.

5. The method according to claim 4 wherein A is carbon; and wherein R is —CH$_2$CH$_3$ and $R^1$ is —CH$_3$; or R is —CH$_2$CH$_2$CH$_3$ and $R^1$ is —CH$_2$CH$_2$CH$_2$OCH$_3$; or R is —CH$_2$CH$_3$ and $R^1$ is —CH$_2$CH$_2$CH$_3$; or R is —CH$_2$CH$_2$(CH$_3$)$_2$ and $R^1$ is hydrogen; or R is —CH$_2$CH$_3$ and $R^1$ is —CH$_2$OCH$_2$CH$_3$; and carbons 4 and 6 of the topical carbonic anhydrase inhibitor both have S absolute stereochemical configuration.

6. The method according to claim 5 wherein the carbonic anhydrase inhibitor is selected from the group consisting of dorzolamide, brinzolamide, acetazolamide, metazolamide and the like.

7. The method according to claim 6 wherein the carbonic anhydrase inhibitor is dorzolamide.

8. The method according to claim 7 wherein the dorzolamide is (S,S)-(–)-5,6-dihydro-4-ethylamino-6-methyl-4H-thieno[2,3-b]thiopyran-2-sulfonamide-7,7-dioxide hydrochloride.

9. The method of claim 2 wherein the concentration of carbonic anhydrase inhibitor is about 0.5 to about 2.0% (w/w) and the concentration of xanthan gum is 0.4 to 0.7% (w/w).

10. The method of claim 2 wherein the composition wherein the hypotonic solution has a freezing point depression of between –0.28° C. and –0.4° C. and the hypotonicity of the solution is between 150 and 215 mOs/kg.

11. The method according to claim 1 which additionally comprises about 0.01 to 1% (w/w) of a β-adrenergic receptor blocking agent, or an ophthalmologically acceptable salt thereof.

12. The method according to claim 11 wherein the concentration of β-adrenergic receptor blocking agent is about 0.1 to 0.5% (w/w).

13. The method according to claim 12 wherein the β-adrenergic receptor is timolol maleate.

14. The method according to claim 2 which additionally comprises about 0.01 to 1% (w/w) of a β-adrenergic receptor blocking agent, or an ophthalmologically acceptable salt thereof.

15. The method according to claim 14 wherein the concentration of β-adrenergic receptor blocking agent is about 0.1 to 0.5% (w/w).

16. The method according to claim 15 wherein the β-adrenergic receptor is timolol maleate.

17. The method according to claim 12 which additionally comprises about 0.005 to 2.0% (w/w) of a prostaglandin, prostaglandin derivative, or an ophthalmologically acceptable salt thereof.

18. The method according to claim 17 wherein the concentration of prostaglandin or prostaglandin derivative is about 0.1 to 1% (w/w).

19. The method according to claim 18 wherein the prostaglandin, prostaglandin derivative is:
11-pivaloyl prostaglandin F2α hydroxyethyl ester,
(+)-(Z)-sodium-7-[1R, 2R, 3R, 5S)-3,5-dihydroxy-2-[(E)-1-octenyl]cyclopentyl]-5-heptenoate sesquihydrate,
[1α,2β,3α,5α]methyl-5-cis-2-(phenylethylsulfonamidomethyl)-3,5-dihydroxycyclopentyl heptenoate,
(+–)-5-[6-(1-hydroxy)hexyl)-1,3-benzodioxol-5-yl]-pentanol, 15-pivaloyl PGFα,
7-[3α,5α dihydroxy-2-(3a-hydroxy-5--1E-pentenyl) cyclopentyl]-5Z-heptenoic acid,
isopropyl (Z)-7-[(1R,2R,3R,5S)-3,5-dihydroxy-2-[(3R)-3-hydroxy-5-phenylpentyl]cyclopentyl]-5-heptenoate or
13,14-dihydro-15-keto-20-ethyl-PGF2α isopropyl ester trimethylphenol-1-acetate.

20. The method according to claim 19 wherein the prostaglandin or prostaglandin derivative isopropyl (Z)-7-[(1R, 2R,3R,5S)-3,5-dihydroxy-2-[(3R)-3-hydroxy-5-phenylpentyl]cyclopentyl]-5-heptenoate, (+)-(Z)-sodium-7-[1R, 2R, 3R, 5S)-3,5-dihydroxy-2-[(E)-1-octenyl] cyclopentyl]-5-heptenoate sesquihydrate, or 13,14-dihydro-15-keto-20-ethyl-PGF2α isopropyl ester trimethylphenol-1-acetate.

* * * * *